United States Patent [19]
Inomata et al.

[11] Patent Number: 5,322,557
[45] Date of Patent: Jun. 21, 1994

[54] PRIMER COMPOSITIONS

[75] Inventors: Hiroshi Inomata, Annaka; Yasuo Tarumi, Takasaki; Kazuhiko Tomaru, Annaka, all of Japan

[73] Assignee: Shin-Etsu Chemical Co., Ltd., Tokyo, Japan

[21] Appl. No.: 994,990

[22] Filed: Dec. 22, 1992

[30] Foreign Application Priority Data

Dec. 24, 1991 [JP] Japan .................... 3-356413

[51] Int. Cl.$^5$ ............................ C09K 3/00
[52] U.S. Cl. ............... 106/287.14; 106/287.13; 106/287.15; 556/400; 556/436; 556/437
[58] Field of Search ......... 106/14.41, 287.15, 287.13, 106/287.14; 556/400, 436, 437

[56] References Cited

U.S. PATENT DOCUMENTS

| | | | |
|---|---|---|---|
| 4,098,749 | 7/1978 | Hoshino et al. | 106/14.41 |
| 4,174,228 | 11/1979 | Boberiski et al. | 106/18.21 |
| 4,179,426 | 12/1979 | Steinbach et al. | 106/287.15 |
| 4,324,712 | 4/1982 | Vaugh, Jr. | 106/287.15 |
| 4,689,085 | 8/1987 | Plueddemann | 106/287.15 |
| 4,749,741 | 6/1988 | Saito et al. | 106/287.15 |
| 5,101,057 | 3/1992 | Satoh et al. | 556/437 |
| 5,187,014 | 2/1993 | Suzaki et al. | 106/287.15 |

FOREIGN PATENT DOCUMENTS

| | | | |
|---|---|---|---|
| 0061871 | 10/1982 | European Pat. Off. | 106/287.15 |
| 0485985 | 5/1992 | European Pat. Off. | |
| 4024720 | 2/1991 | Fed. Rep. of Germany | |

*Primary Examiner*—Anthony Green
*Attorney, Agent, or Firm*—Birch, Stewart, Kolasch & Birch

[57] ABSTRACT

A primer composition comprising (A) a fluorinated alkoxysilane containing an epoxy group, (B) an organic titanium or aluminum compound, and (C) a solvent is effective in bonding fluorinated organic polymers to metal and glass members.

13 Claims, No Drawings

PRIMER COMPOSITIONS

BACKGROUND OF THE INVENTION

1. Field of the Invention

This invention relates to a primer composition that forms a strong long-lasting bond to fluorinated materials and is thus suitable as an adhesive for composite materials containing fluorinated materials.

2. Prior Art

Composite materials having organic polymers such as rubber and plastics bonded to inorganic materials such as metals and glass are of greater value in these years. A key for such composite materials to perform well is a strong long-lasting bond between two types of materials.

Among many prior art primer compositions for bonding organic polymers to inorganic materials, compositions predominantly comprising an organic silicon compound having an alkoxysilyl group and an epoxy group in a molecule are known to be effective. More particularly, a primer composition predominantly comprising an organic silicon compound of the following formula (2):

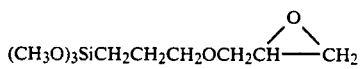

(2)

was proposed as effective for bonding silicone rubber to metals and plastics.

These primer compositions, however, were insufficient in adhesion to fluorinated organic polymers such as fluorinated silicone rubbers and fluoro-resins and less satisfactory in moisture resistance and water resistance. The primer composition based on a compound of formula (2) could not retain adhesion over a desired service life.

SUMMARY OF THE INVENTION

Therefore, an object of the present invention is to provide a primer composition capable of forming a strong and long-lasting bond to fluorinated organic polymers and thus useful as an adhesive for composite materials containing fluorinated materials.

According to the present invention, there is provided a primer composition comprising (A) a fluorinated alkoxysilane containing an epoxy group of the general formula (1).

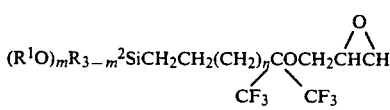

(1)

In formula (1), $R^1$ and $R^2$ are independently monovalent organic groups, letter m is an integer of 1 to 3 and n is equal to 0 or 1. The composition further includes (B) an organic titanium and/or aluminum compound and (C) a solvent. This primer composition is effective in bonding fluorinated silicone rubbers, fluoro-resins and other fluorinated organic polymers to inorganic materials and forms a long-lasting bond such that the adhesion is on slightly reduced even when stored in a hot humid atmosphere.

More particularly, the alkoxysilane of formula (1) is well compatible with fluorinated materials due to the presence of two —$CF_3$ groups in its molecule so that the bonding functional groups (alkoxysilyl and epoxy groups) may act more efficiently. At the same time, the —$CF_3$ groups render the primer molecule more hydrophobic so that the primer may form a more durable bond. Therefore, the primer composition of the invention offers improved adhesion properties including strength and retention of a bond and is useful as an adhesive for composite materials containing fluorinated materials.

DETAILED DESCRIPTION OF THE INVENTION

A first essential component of the primer composition according to the present invention is (A) a fluorinated alkoxysilane containing an epoxy group. This alkoxysilane is of the general formula (1):

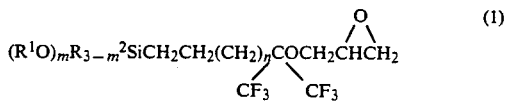

(1)

wherein $R^1$ and $R^2$ are independently monovalent organic groups, letter m is an integer of 1 to 3 and n is equal to 0 or 1.

Exemplary groups represented by $R^1$ in formula (1) include an alkyl group having 1 to 10 carbon atoms such as methyl, ethyl, n-propyl, i-propyl and n-butyl groups, a fluoroalkyl group having 2 to 15 carbon atoms such as a trifluoroethyl group, an acyl group such as acetyl and propionyl groups, and an alkenyl group having 2 to 15 carbon atoms such as an isopropenyl group, with the methyl and ethyl groups being preferred. Exemplary groups represented by $R^2$ include an alkyl group having 1 to 10 carbon atoms such as methyl, ethyl and n-propyl groups, an aryl group having 6 to 10 carbon atoms such as a phenyl group, and a fluoroalkyl group having 3 to 15 carbon atoms such as a trifluoropropyl group, with the methyl group being preferred. Letter m is an integer of 1 to 3, especially 2 or 3, and n is equal to 0 or 1.

Some illustrative, non-limiting examples of the alkoxysilane of formula (1) are given below.

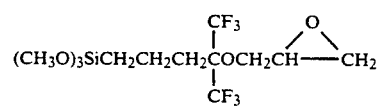

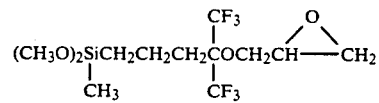

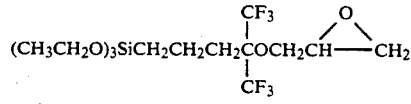

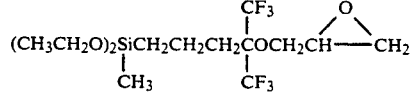

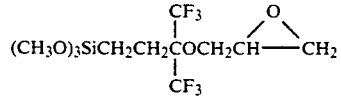

-continued

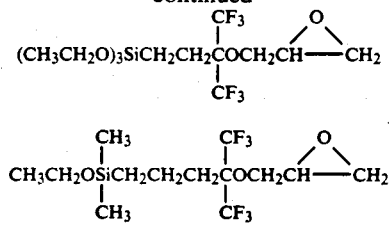

The compounds of formula (1) are novel compounds. They can be synthesized by addition reaction between a fluorinated unsaturated glycidyl ether of formula (A) and a hydrosilane of formula (B) in the presence of a transition metal catalyst.

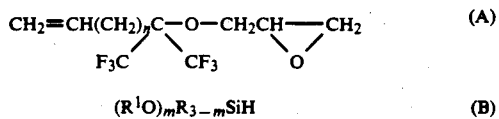

$(R^1O)_mR_{3-m}SiH$ (B)

The fluorinated unsaturated glycidyl ether of formula (A) are also novel. They may be prepared by reacting a corresponding alcohol and epichlorohydrin in accordance with the following scheme.

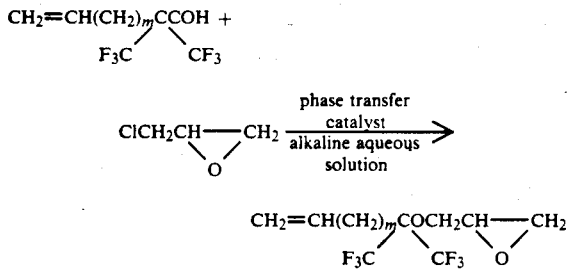

Typical examples are glycidyl ethers of the following formulae (A-1) and (A-2).

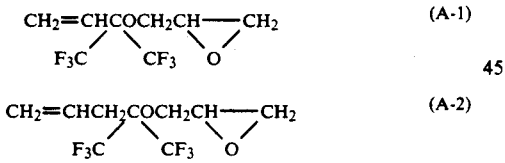

The compound of formula (A-1) is prepared by reaction between 1,1,1-trifluoro-2-trifluoromethyl-3-buten-2-ol and chloromethyloxirane. The compound of formula (A-2) is prepared by reaction between 1,1,1-trifluoro-2-trifluoromethyl-4-penten-2-ol and chloromethyloxirane. Reaction is carried out in a two phase system consisting of a basis aqueous phase and an organic phase using a phase transfer catalyst in the form of a quaternary ammonium salt or quaternary phosphonium salt.

For addition reaction, the fluorinated unsaturated glycidyl ether of formula (A) and the hydrosilane of formula (B) are preferably used in a molar ratio of from 1:0.8 to 1:2, more preferably from 1:1 to 1:1.5. This reaction is carried out in the presence of a catalyst which may be a transition metal such as Pt, Rh and Pd, a transition metal salt, a transition metal complex or a mixture thereof. Examples of the catalyst include chloroplatinic acid (H$_2$PtCl$_6$), complexes of chloroplatinic acid with olefins, complexes of chloroplatinic acid with alcohols, complexes of chloroplatinic acid with vinylsiloxanes, RhCl$_3$, Rh(CH$_3$COCHCOCH$_3$)$_3$, Rh(PPh$_3$)$_3$Cl, Rh(PPh$_3$)$_3$Br, Rh$_2$ (AcO)$_4$, Rh(PPh$_3$)$_2$(CO)Cl, Rh($\eta^4$—C$_7$H$_8$)Cl, Rh(CH$_3$COCHCOCH$_3$) (CO)$_2$, Rh$_4$(CO)$_{12}$, Rh$_6$(CO)$_{16}$, Rh(PPh$_3$)$_3$(CO)H, (NH$_4$)$_2$PdCl$_6$, (NH$_4$)$_2$PdCl$_4$, Pd(CH$_3$COCHCOCH$_3$)$_2$, Pd(PhCN)$_2$Cl$_2$, Pd(PPh$_3$)$_2$Cl$_2$, and Pd(PPh$_3$)$_4$ wherein Ph represents a phenyl group.

The reaction may be carried out in a solvent although it smoothly proceeds in a solventless system. The reaction temperature is usually 30° to 200° C., preferably 60° to 150° C. and the reaction time is usually 30 minutes to 48 hours. The reaction can be tracked by gas chromatography for monitoring the consumption of the reactants and production of an end product. If the reactant consumption is interrupted midway the reaction process, the reaction can be re-started by supplementing the catalyst. The product can be purified and isolated by distillation.

A second essential component of the primer composition according to the present invention is (B) an organic titanium compound or an organic aluminum compound, which is effective as an adhesion promoter.

Preferred organic titanium compounds are those having a structure in which a titanium atom and an organic group are connected through a Ti—O—C linkage. Examples are given below.

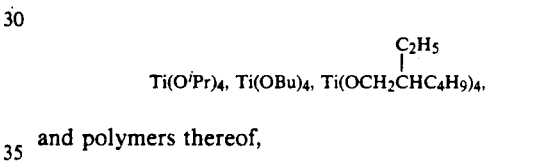

and polymers thereof,

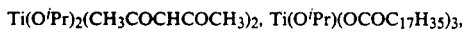

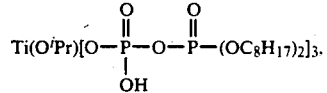

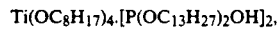

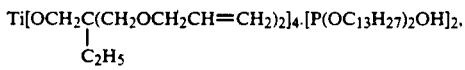

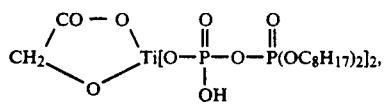

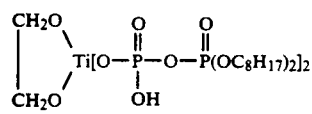

In the formulae, $^i$Pr is an isopropyl group and Bu is a butyl group.

Preferred among these are Ti(O$^i$Pr)$_4$, Ti(OBu)$_4$ and polymers thereof.

Preferred organic aluminum compounds are aluminum alcolates and aluminum chelates. Examples are given below.

Al(O$^i$Pr)$_3$, Al(O$^i$Pr)$_2$(O$^{sec}$Bu),
Al(O$^i$Pr)$_2$(CH$_3$COCHCOOC$_2$H$_5$),
Al(CH$_3$COCHCOOC$_2$H$_5$)$_3$,
Al(OC$_4$H$_9$)$_2$(CH$_3$COCHCOOC$_2$H$_5$), Al(OCH4H9)(CH3COCHCOOC2H5)2

In the formulae, iPr is an isopropyl group and secBu is a secondary butyl group.

The organic titanium and aluminum compounds may be used alone or in admixture of two or more. Preferably the organic titanium or aluminum compound is used in an amount of 5 to 200 parts, more preferably 10 to 100 parts by weight per 100 parts by weight of the fluorinated alkoxysilane of formula (1). Heat resistance is sometimes low with less than 5 parts on this basis of the organic titanium or aluminum compound whereas more than 200 parts of the organic titanium or aluminum compound would adversely affect adhesion.

A third essential component is a solvent which includes aromatic hydrocarbons such as toluene and xylene, aliphatic hydrocarbons such as n-hexane, alcohols such as methanol, ethanol and isopropanol, fluorinated aromatic hydrocarbons such as benzotrifluoride, meta-xylenehexafluoride and para-xylenehexafluoride, fluorinated alcohols such as trifluoroethanol and hexafluoroisopropanol, and perfluoroethers such as perfluorobutyltetrahydrofuran.

The solvent is used in an amount of 1 to 100 parts by weight per one part by weight of the fluorinated alkoxysilane of formula (1).

It is sometimes useful to add to the primer composition of the invention, another optional component, for example, an alkoxysilane other than that of formula (1), as exemplified by the following formulae.

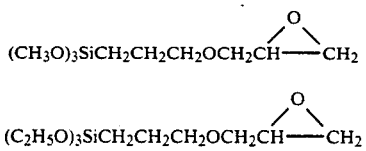

There has been described a primer composition which is effective for bonding fluorinated silicone rubbers, fluoro-resins and other fluorinated organic polymers to inorganic materials and forming a long-lasting bond in that it does little lower its adhesion even when stored in a hot humid atmosphere. The composition is thus a useful adhesive for composite materials containing fluorinated materials.

EXAMPLE

Examples of the present invention are given below by way of illustration and not by way of limitation. All parts are by weight.

EXAMPLE AND COMPARATIVE EXAMPLE

A primer composition designated I was prepared by evenly mixing 5 parts of a fluorinated alkoxysilane containing an epoxy group of formula (3), 1 part of Ti(O-Bu)4, and 50 parts of meta-xylenehexafluoride

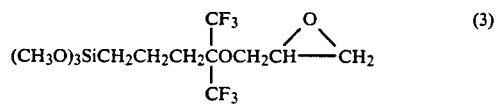

For comparison purposes, a primer composition designated II was prepared by evenly mixing 5 parts of an alkoxysilane containing an epoxy group of formula (2), 1 part of Ti(OBu)4, and 50 parts of meta-xylenehexafluoride

Primer compositions I and II were examined for adhesion by the following procedure. The results are shown in Table 1.

Adhesion test

Each primer composition was coated to a stainless steel plate of 25 mm×100 mm×0.3 mm in a coating weight of 30 g/m² and air dried for 30 minutes. A 2-mm thick sheet of a fluorosilicone rubber composition in the form of fluorosilicone rubber compound FE241 (commercially available from Shin-Etsu Chemical Co., Ltd.) containing 0.8% by weight of a vulcanizing agent Perhexa 25B (2,5-dimethyl-2,5-di-t-butylperoxyhexane, commercially available from Nippon Oil & Fats Co., Ltd.) was placed in close contact with the primer coating, heated at 165° C. under a pressure of 30 kg/cm² for 10 minutes, and further heated at 200° C. for 4 hours for curing. There was obtained an adhesion test piece in which the fluorosilicone rubber was bonded to the stainless steel plate through the primer coating.

The test piece was examined for adhesion both at the initial and after storage at 150° C. and RH 90% for 3 or 10 days and evaluated in accordance with the following criterion.
○: good bond
Δ: partially peeled
X: peeled

TABLE 1

|  | Primer composition | |
| --- | --- | --- |
|  | I | II |
| Initial | ○ | Δ |
| 150° C./RH90%/3 days | ○ | X |
| 150° C./RH90%/10 days | ○ | X |

As is evident from Table 1, the primer composition within the scope of the invention is improved in adhesion and adhesion durability. Similar results were obtained when the primer compositions were coated to soft steel and aluminum plates instead of the stainless steel plate and examined by the same adhesion test.

REFERENCE EXAMPLE 1

A 500-ml three-necked flask equipped with a condenser, dropping funnel, thermometer and magnetic stirrer was charged with 108.5 grams (0.55 mol) of 1,1,1-trifluoro-2-trifluoromethyl-3-buten-2-ol, 254.4 grams (2.75 mol) of chloromethyloxirane, and 18.7 grams (0.055 mol) of tetrabutyl ammonium hydrogen sulfate. With stirring, the flask was heated to 70° C. Then 146.7 grams (0.55 mol) of a 14% sodium hydroxide aqueous solution was added dropwise over about 1.5 hours and agitation continued for a further 30 minutes. The reaction solution was allowed to cool down to room temperature, whereupon the organic phase was separated from the aqueous phase, washed with water twice, and then dried over 30.0 grams of anhydrous sodium sulfate. After excess chloromethyloxirane was distilled off, vacuum distillation yielded 89.4 grams of the fluorinated allyl glycidyl ether of formula (2a). It had a boiling point of 81° to 82° C./65 Torr and a yield of 65.0%.

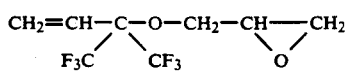 (2a)

This fluorinated allyl glycidyl ether was examined by proton NMR spectroscopy, IR spectroscopy, mass spectroscopy and elemental analysis.

$^1$H-NMR (CCl$_4$ solution, TMS internal standard, ppm):

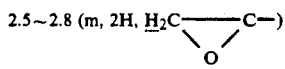

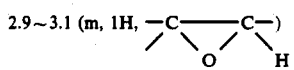

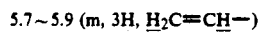

IR (KBr plate method, neat, cm$^{-1}$): 3010, 2940, 1920, 1645, 1465, 1435, 1410, 1300–1150, 1030, 960, 915, 860, 735

MS (m/e): 251 (M+1), 233, 221, 73

| | Elemental analysis: | | |
|---|---|---|---|
| | C | H | F |
| Calcd. (%) | 38.4 | 3.2 | 45.6 |
| Found (%) | 38.6 | 3.1 | 45.4 |

Next, a 100-ml pressure-resistant stainless steel cylinder was charged with 25.0 grams (0.10 mol) of the compound of formula (2a), 14.7 grams (0.12 mol) of (CH$_3$O)$_3$SiH, and 0.024 grams (6.0×10$^{-5}$ mol) of Rh(CH$_3$COCHCOCH$_3$)$_3$ and heated at 135° C. for 10 hours. Then 7.3 grams (0.06 mol) of (CH$_3$O)$_3$SiH and 0.024 grams (6.0×10$^{-5}$ mol) of Rh(CH$_3$COCH-COCH$_3$)$_3$ were added to the reactor, which was heated at 135° C. for a further 10 hours. Distillation of the reaction mixture provided 22.0 grams of a product. On analysis, it was identified to be the compound of formula (1a). The yield was 59%.

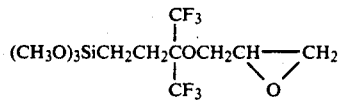 (1a)

Analysis $^{19}$F-NMR (CF$_3$COOH standard): 4.9 ppm (s)
$^1$H-NMR (TMS standard):

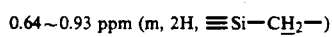

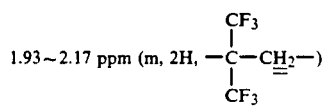

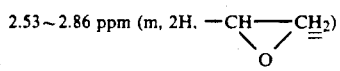

-continued

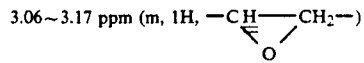

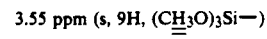

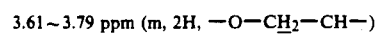

IR (cm$^{-1}$): 3060 (w), 2955 (s), 2850 (s), 1458 (m), 1280 (s), 1210 (s), 1085 (s), 827 (s)

| | Elemental analysis: | | | |
|---|---|---|---|---|
| | C | H | F | Si |
| Calcd. (%) | 35.48 | 4.87 | 30.61 | 7.54 |
| Found (%) | 35.02 | 4.81 | 31.15 | 7.99 |

REFERENCE EXAMPLE 2

A 300-ml four-necked flask equipped with a condenser, dropping funnel, thermometer and magnetic stirrer was charged with 43.3 grams (0.208 mol) of 1,1,1-trifluoro-2-trifluoromethyl-4-penten-2-ol, 96.2 grams (1.04 mol) of epichlorohydrin, and 7.1 grams (0.021 mol) of tetrabutyl ammonium hydrogen sulfate. With stirring, the flask was heated to 85° C. Then 55.5 grams (0.208 mol) of a 15% sodium hydroxide aqueous solution was added dropwise over about 30 minutes and agitation continued at 85° C. for a further 30 minutes. The organic phase (lower layer) was separated from the reaction mixture, washed with water twice, and then dried over anhydrous sodium sulfate. Vacuum distillation of this mixture yielded 38.7 grams of a fraction having a boiling point of 88° to 90° C. /47 mmHg. Based on the analytical results shown below, it was identified to be the fluorinated unsaturated glycidyl ether of formula (2b). The yield was 70%.

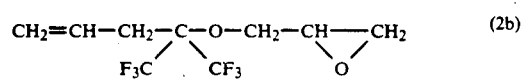 (2b)

$^{19}$F-NMR (CCl$_4$ solution, CF$_3$COOH standard): 4.3 ppm(s)

$^1$H-NMR (CCl$_4$ solution, TMS standard):

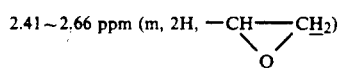

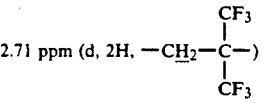

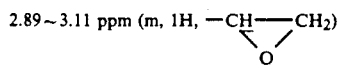

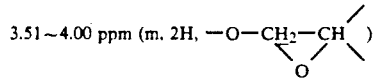

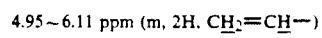

| Elemental analysis: | | | |
|---|---|---|---|
| | C | H | F |
| Calcd. (%) | 40.92 | 3.82 | 43.15 |
| Found (%) | 40.98 | 3.75 | 43.71 |

Next, a 200-ml three-necked flask equipped with a reflux condenser, dropping funnel, thermometer an magnetic stirrer was charged with 26.4 grams (0.10 mol) of the compound of formula (2b) and 0.011 grams $(2.8 \times 10^{-5}$ mol) of $Rh(CH_3COCHCOCH_3)_3$ and heated at 80° C. Then 17.1 grams (0.14 mol) of $(CH_3O)_3SiH$ was added over 2 hours to the flask, which was heated at 80° C. for a further 15 hours. Distillation of the reaction mixture provided 25.5 grams of a product. On analysis, it was identified to be the compound of formula (1b). The yield was 66%.

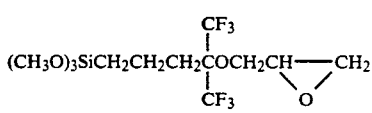

Analysis $^{19}$F-NMR ($CF_3COOH$ standard): 4.7 ppm (s)
$^1$H-NMR (TMS standard):

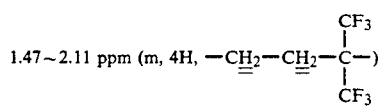

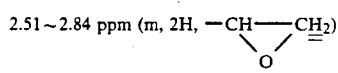

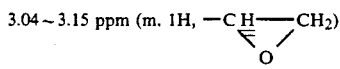

3.55 ppm (s, 9H, $(C\underline{H}_3O)_3Si—$)

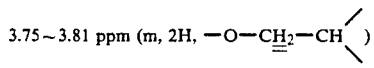

IR (cm$^{-1}$): 3060 (w), 2955 (s), 2850 (s), 1464 (m), 1274 (s), 1210 (a), 1090 (s), 818 (s)

| Elemental analysis: | | | | |
|---|---|---|---|---|
| | C | H | F | Si |
| Calcd. (%) | 37.30 | 5.22 | 29.50 | 7.27 |
| Found (%) | 36.98 | 5.10 | 28.85 | 7.51 |

REFERENCE EXAMPLE 3

By reacting 26.4 grams (0.10 mol) of the compound of formula (2b) with 14.6 grams (0.14 mol) of a compound of formula (3a) shown below in the same manner as in Reference Example 2, 21.4 grams of a compound of formula (1c) was obtained. The yield was 58%.

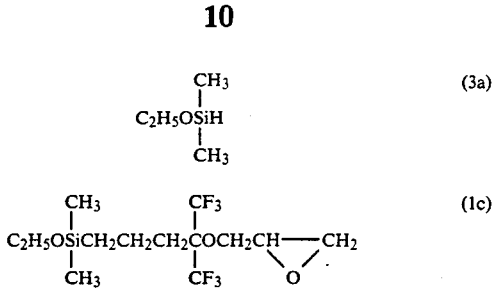

REFERENCE EXAMPLE 4

By reacting 26.4 grams (0.10 mol) of the compound of formula (2b) with 23.0 grams (0.14 mol) Of $(C_2H_5O)_3$-SiH in the same manner as in Reference Example 2, 29.1 grams of a compound of formula (1d) was obtained. The yield was 68%.

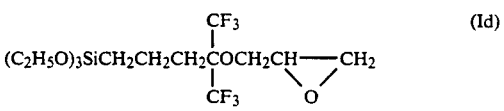

Although some preferred embodiments have been described, many modifications and variations may be made thereto in the light of the above teachings. It is therefore to be understood that within the scope of the appended claims, the invention may be practiced otherwise than as specifically described.

We claim:

1. A primer composition comprising (A) 100 parts by weight of a fluorinated alkoxysilane having an epoxy group of the general formula:

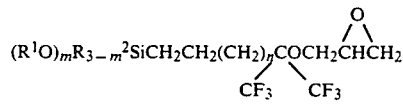

wherein R$^1$ is selected from the group consisting of an alkyl group having 1 to 10 carbon atoms, a fluoroalkyl group having 2 to 15 carbon atoms, an acyl group, and an alkenyl group having 2 to 15 carbon atoms, R$^2$ is selected from the group consisting of an alkyl group having 1 to 10 carbon atoms, an aryl group having 6 to 10 carbon atoms, and a fluoroalkyl group having 3 to 15 carbon atoms, letter m is an integer of 1 to 3 and n is equal to 0 or 1, (B) 5–200 parts by weight of an organic titanium compound having a Ti—O—C linkage, an aluminum alcolate, an aluminum chelate or a mixture thereof, and (C) 100–10,000 parts by weight of a solvent.

2. A primer composition according to claim 1 wherein in formula (1), R$^1$ is a methyl or ethyl group, R$^2$ is a methyl group, and letter m is equal to 2 or 3.

3. A primer composition according to claim 1, wherein R$^1$ is selected from the group consisting of methyl, ethyl, n-propyl, i-propyl, n-butyl, trifluoroethyl, acetyl, propionyl, and isopropenyl.

4. A primer composition according to claim 1, wherein R$^2$ is selected from the group consisting of methyl, ethyl, n-propyl, phenyl, and trifluoropropyl.

5. A primer composition according to claim 1, wherein said fluorinated alkoxysilane of formula (1) is selected from the group consisting of:

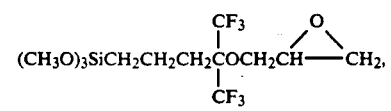

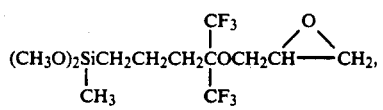

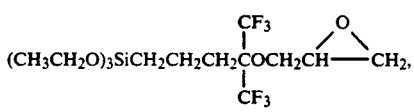

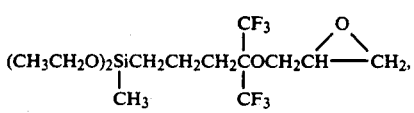

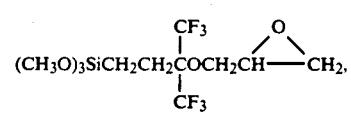

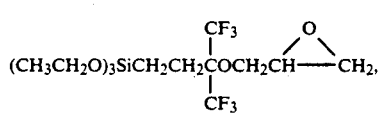

and

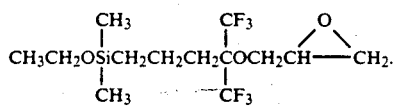

6. A primer composition according to claim 1, wherein said component (B) is an organic titanium compound selected from the group consisting of

and polymers thereof, wherein $^{i}$Pr represents an isopropyl group and Bu represents a butyl group.

7. A primer composition according to claim 6, wherein said organic titanium compound is selected from the group consisting of Ti(O$^{i}$Pr)$_4$, Ti(OBu)$_4$, and polymers thereof.

8. A primer composition according to claim 1, wherein said component (B) is an organic titanium compound selected from the group consisting of

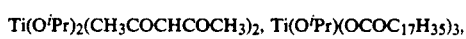

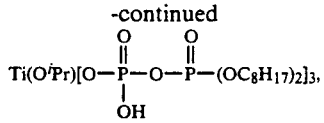

$Ti(OC_8H_{17})_4\cdot[P(OC_{13}H_{27})_2OH]_2$,

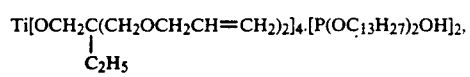

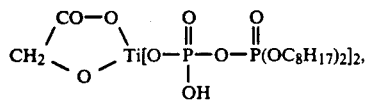

and

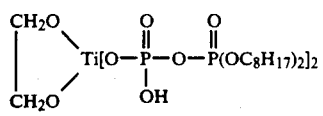

wherein $^{i}$Pr represents an isopropyl group and Bu represents a butyl group.

9. A primer composition according to claim 1, wherein said component (B) is an aluminum alcolate or an aluminum chelate selected from the group consisting of:

Al(O$^{i}$Pr)$_3$, Al(O$^{i}$Pr)$_2$(O$^{sec}$Bu),
Al(O$^{i}$Pr)$_2$(CH$_3$COCHCOOC$_2$H$_5$),
Al(CH$_3$COCHCOOC$_2$H$_5$)$_3$,
Al(OC$_4$H$_9$)$_2$(CH$_3$COCHCOOC$_2$H$_5$), and
Al(OC$_4$H$_9$)(CH$_3$COCHCOOC$_2$H$_5$)$_2$ wherein $^{i}$Pr represents an isopropyl group and $^{sec}$Bu represents a secondary butyl group.

10. A primer composition according to claim 1, wherein said component (B) is contained in an amount of 10 to 100 parts by weight.

11. A primer composition according to claim 1, wherein said solvent is selected from the group consisting of aromatic hydrocarbons, aliphatic hydrocarbons, alcohols, fluorinated aromatic hydrocarbons, fluorinated alcohols, and perfluoroethers.

12. A primer composition according to claim 11, wherein said solvent is selected from the group consisting of toluene, xylene, n-hexane, methanol, ethanol, isopropanol, benzotrifluoride, meta-xylenehexafluoride, para-xylenehexafluoride, trifluoroethanol, hexafluoroisopropanol, and perfluorobutyltetrahydrofuran.

13. A primer composition according to claim 1, further comprising

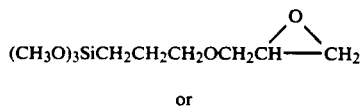

or

* * * * *